United States Patent [19]

Logé et al.

[11] Patent Number: 4,589,847

[45] Date of Patent: May 20, 1986

[54] TARTAR-REMOVING DENTAL HANDPIECE

[75] Inventors: Hans Logé; Eugen Eibofner, both of Biberach; Walter Mössle, Bad Waldsee, all of Fed. Rep. of Germany

[73] Assignee: Kaltenbach & Voight GmbH & Co., Biberach, Fed. Rep. of Germany

[21] Appl. No.: 638,635

[22] Filed: Aug. 7, 1984

[30] Foreign Application Priority Data

Aug. 8, 1983 [DE] Fed. Rep. of Germany ....... 3328605

[51] Int. Cl.⁴ .............................................. A61C 1/08
[52] U.S. Cl. .................................... 433/126; 433/118; 433/120
[58] Field of Search ............... 433/126, 118, 119, 120, 433/82

[56] References Cited

U.S. PATENT DOCUMENTS

| 3,930,173 | 12/1975 | Banko | 433/119 |
| 4,080,737 | 3/1978 | Fleer | 433/126 |
| 4,217,101 | 8/1980 | Loge | 433/82 |
| 4,219,619 | 8/1980 | Zarow | 433/118 |
| 4,260,380 | 4/1981 | Nash | 433/119 |
| 4,303,392 | 12/1981 | Rollofson | 433/126 |
| 4,403,959 | 9/1983 | Hatakeyama | 433/82 |

FOREIGN PATENT DOCUMENTS

| 2905035 | 3/1975 | Fed. Rep. of Germany | 433/119 |
| 3034930 | 6/1982 | Fed. Rep. of Germany | 433/119 |
| 3215189 | 9/1982 | Fed. Rep. of Germany | 433/119 |
| 7729110 | 5/1983 | Fed. Rep. of Germany | 433/119 |

Primary Examiner—John J. Wilson
Attorney, Agent, or Firm—Scully, Scott, Murphy & Presser

[57] ABSTRACT

A tartar-removing dental handpiece, consisting of an elongated gripping sleeve on which there is arranged a vibration generator, which is connected to a vibratable tartar-removing instrument arranged at one end of the gripping sleeve for transmitting vibrations thereto. The gripping sleeve incorporates at least one medium supply conduit which is connected through a coupling member located at the end of the gripping sleeve distant from the instrument to a connecting conduit leading to a medium source.

14 Claims, 5 Drawing Figures

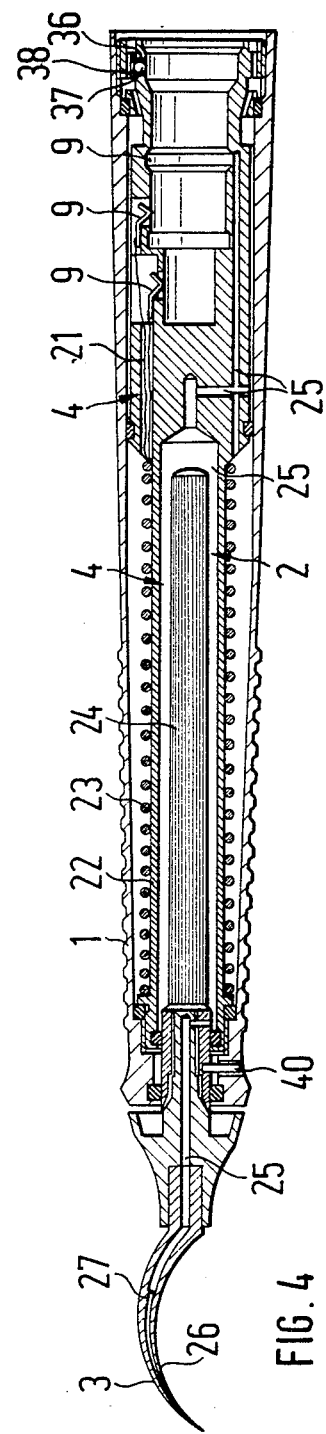
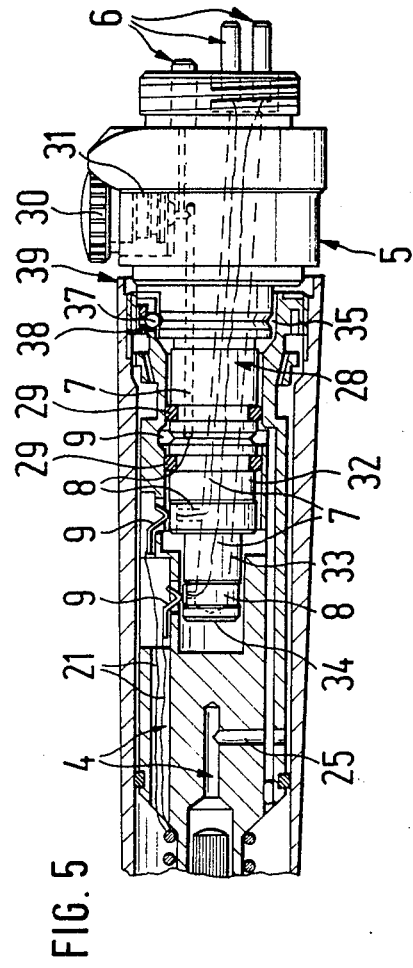
FIG. 4
FIG. 5

TARTAR-REMOVING DENTAL HANDPIECE

BACKGROUND OF THE INVENTION

1. Field of the Invention

The present invention relates to a tartar-removing dental handpiece, consisting of an elongated gripping sleeve on which there is arranged a vibration generator, which is connected to a vibratable tartar-removing instrument arranged at one end of the gripping sleeve for transmitting vibrations thereto, wherein the gripping sleeve incorporates at least one medium supply conduit which is connected through a coupling member located at the end of the gripping sleeve distant from the instrument to a connecting conduit leading to a medium source.

2. Discussion of the Prior Art

A tartar-removing dental handpiece of that type has become known, for example, from the disclosure of European Patent Application No. 28 531. In this known dental handpiece, the coupling member is fixedly connected with the gripping sleeve through a screw thread connection. When the treating person effectuates rotating movements about the axis of the handpiece, which are necessary during treatment for the removal of tartar, then these rotational movements are hemmed by the relatively rigid connecting conduits leading to the medium source, which are mostly combined within a hose, and which is extremely tiring for the treating person. In addition thereto, for a separation between the gripping sleeve and the coupling, member it is necessary to effect a time-consuming loosening of the screw-threaded connection.

SUMMARY OF THE INVENTION

Accordingly, in order to obviate a ameliorate the disadvantages encountered in the prior art, the present invention provides for a handpiece structure which facilitates for an unhindered and unrestricted rotatability of the gripping sleeve, and concurrently allows for a rapid separation and assembling of the gripping sleeve and coupling member.

The advantages which are achieved through the use of the invention can be essentially ascertained in that through the freely rotatable quick-connect coupling, there is achieved a rapid separation and assembly for the gripping sleeve and coupling member, as well as an unhindered and unrestricted rotatability between the gripping sleeve and the coupling member, whereby in every position of rotation there is ensured a satisfactory media transfer between the coupling member and the gripping sleeve.

From the disclosure of German Petty Patent No. 77 29 110 there has become known a dental handpiece which there is also formed a freely rotatable quick-connect coupling by the coupling member with respect to the gripping sleeve, wherein the quick-connect coupling and the end of the gripping sleeve which is distant from the instrument are provided with media transfer means which are operative in every position of rotation. However, this known handpiece pertains to a completely different constructional class; thus, it does not relate to a tartar-removing dental handpiece, and in the gripping sleeve thereof no provision is made for a vibration generator for a vibratable tartar-removing instrument. Contrastingly, in the known prior art handpiece a drive assembly is provided at one end of the gripping sleeve, which is constructed as an air turbine for the direct drive of a rotatable dental treatment instrument.

BRIEF DESCRIPTION OF THE DRAWINGS

Reference may now be had to the following detailed description of exemplary embodiments of the invention, taken in conjunction with the accompanying drawings; in which:

FIG. 4 illustrates a longitudinal sectional view of a tartar-removing dental handpiece with an electrically operable vibration generator; and FIG. 5 illustrates the right-hand end of the tartar-removing dental handpiece of FIG. 4, shown on an enlarged scale, with an inserted guide trunnion of a coupling member.

DETAILED DESCRIPTION

Figure 1:
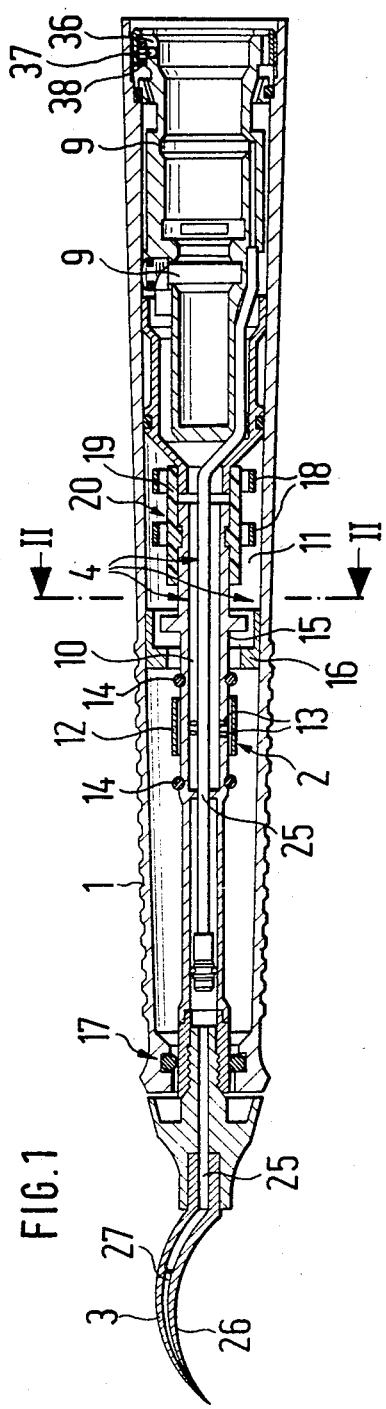
FIG. 1 illustrates a longitudinal sectional view through a tartar-removing dental handpiece with a pneumatically operable vibration generator.

The tartar-removing dental handpiece is constituted of an elongated round gripping sleeve 1 within which there is arranged a vibration generator 2 which, in order to set a tartar-removing instrument 3 which is vibratably supported at one end of the gripping sleeve 1, into vibrations, is connected to the instrument 3 for transmitting vibrations thereto. The gripping sleeve 1 interiorly thereof possesses at least one medium supply conduit 4, in the illustrative case of FIGS. 1 and 3 constituted of three and in FIGS. 4 and 5 of two media supply conduits. These media supply conduits 4 are connected through coupling conduits 7 of a coupling member 5 located at the end of the gripping sleeve 1 which is distant from the instrument, and also to a connecting conduit 6 leading to a medium source (not shown).

The coupling member 5 is formed as a quick-connect coupling which is freely rotatable, rapidly detachable and rapidly assembliable with respect to the gripping sleeve 1. The quick-connect coupling and the end of the gripping sleeve 1 which is distant from the instrument are provided with medium transfer means 8, 9 which are operative in every position of rotation.

Provided as the medium supply conduit 4 is an energy infeed conduit leading to the vibration generator 2.

Figure 2:
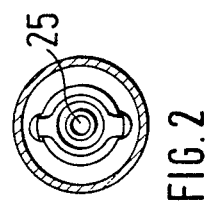
FIG. 2 is a sectional view taken along line II—II in FIG. 1.
Figure 3:
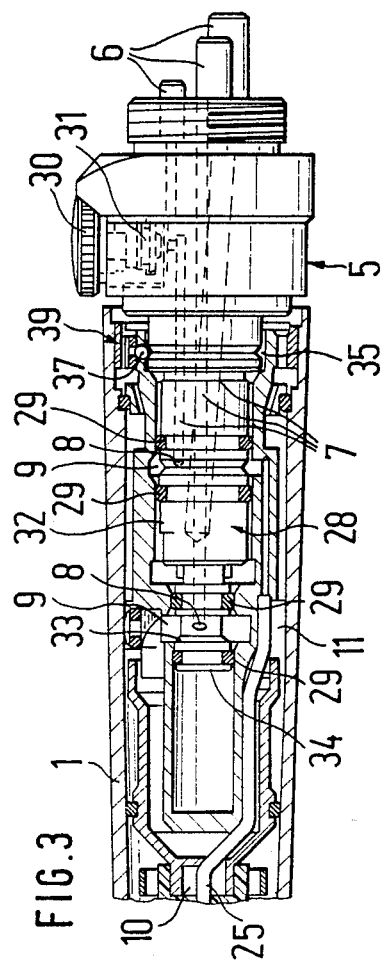
FIG. 3 illustrates the right-hand end of the tartar-removing dental handpiece of FIG. 1, shown on an enlarged scale, with an inserted guide trunnion of a coupling member.

In the case of the embodiment FIGS. 1 through 3, the vibration generator 2 is pneumatically operable, in which the energy infeed conduit is formed by a compressed-air conduit 10. As a further media supply conduit 4 there is provided an exhaust air conduit 11 extending from the vibration generator 2 which, in the region of the vibration generator 2, is formed essentially by the inner space of the gripping sleeve 1. The vibration generator 2, in the embodiment pursuant to FIGS. 1 and 2, consists in the type of European Patent Application No. 28 531 of a sleeve 12 which loosely encompasses the compressed-air conduit 10 and, consequently is thereby radially movable, which is supplied with incoming air through radially directed bores 13 in the compressed-air conduit 10 and thereby set into reciprocatory motion. The impacts which are hereby exerted against the compressed-air conduit 10 produce vibrations which, due to the connection with the tartar-removing instrument 3, are transmitted to the latter. Inasmuch as the sleeve 12 is always located in the region of the bores 13 for the blown-in air, the extent of the axial reciprocating motion of the sleeve 12 is restricted by annular stops 14 which are arranged on the conduit 10. The compressed-air conduit 10 which is settable into vibrations is formed in the type of a resonance member 15. Arranged between the compressed-air conduit 10 and the gripping sleeve 1 is a device 16 for security against rotation, as is illustrated in FIGS. 1 and 2.

The support towards the instrument for the compressed-air conduit 10 which transmits the vibrations is designated by reference numeral 17, and the support distant from the instrument which evidences a connecting hose 19 retained by a loop-like clamping arrangement 18 is designated by reference numeral 20.

In the embodiment pursuant to FIGS. 4 and 5, the vibration generator 2 is electrically operable, wherein the energy supplying conduit is formed by a current line 21. The vibration generator 2 in this embodiment, similar to that in the German AS No. 16 16 127, consists of a tubular support 22 which is positioned coaxially with the gripping sleeve 1, on which there is arranged an exciter winding 23 which is connected with the current line 21. Within the tubular support 22 there is arranged a magnate-strictive converter 24 extending coaxially with the tubular support 22, which is set into vibrations during the supply of current, and these vibrations are transmitted to the instrument 3 which is connected therewith.

Provided as an additional medium supply conduit 4 is a cooling medium conduit 25 leading to the tartar-removing instrument 3. The cooling medium can be air, water or a spray formed from an air-water mixture. The cooling medium conduit 25 connects into the hollow-formed instrument 3, which possesses a cooling medium discharged opening 26 directed towards the treating area. The hollow passageway of the instrument 3 is designated by reference numeral 27.

The coupling member 5 is provided with a guide trunnion 28 which is circular in cross-section and which is insertable into the end of the gripping sleeve 1 distant from the instrument.

The media transfer means are presently formed by discharge openings between two annular sealing elements 29 encompassing the guide trunnion 28 and contacting the gripping sleeve inner wall, which communicate with the connecting passageways connected to the connecting conduit 6, and by means of annular passageways associated with the discharge openings 8, provided in the region of the gripping sleeve inner wall, and which passageways are in communication with the media supply conduits 4.

From FIGS. 4 and 5 there can be ascertained that, when the medium supply conduit is constituted of an electrical current line 21 leading to the vibration generator 2, the medium transfer means are formed by two spaced ring contacts 8 of the connecting conduit 6 which extend about the guide trunnion 28, and by sliding contact 9 of the current line 21 which are provided in the region of the wall of the gripping sleeve and are associated with the ring contacts. In the two lower connecting conduits 6 shown in FIG. 5, this relates to electrical current conductors.

The coupling member 5 possesses at least one regulating member 31 which is equipped with an externally-actuable control element 30, and which is associated with the supply medium conduit 4 which at least serves as cooling medium conduit 25.

As can be ascertained from FIGS. 3 and 5, the guide trunnion 28 incorporates two sections 32, 33 having different diameters which, reduce stepwise towards the free end 34 of the guide trunnion and are contiguous to each other.

Insofar as the elasticity of the sealing element 29 which exerts the clamping force for the retension of the guide trunnion 28 and the gripping sleeve 1 is inadequate, as illustrated there can be provided a latching arrangement 39 for this purpose which retains the guide trunnion 28 into the desired inserted axial position. To this effect, there is formed in the outer wall of the guide trunnion 28 a special latching annular passageway 35, and in the wall of the gripping sleeve 1 there is arranged at least one locking ball 37 supported within a recess 36. The locking ball 37 hereby engages into the latching annular passageway 35 under the action of a spring 38, with the smaller portion of its surface projecting beyond the inner surface of the wall of the gripping sleeve 1. For this purpose, recess 36 includes a bottom surface aligning with the above-mentioned inner surface of the wall of the gripping sleeve 1, which includes an opening which is smaller than the diametral plane of the locking ball 37. During the inserting or the pulling apart procedure, the locking ball 37 is moved out from the latching annular passageway 35 opposite the action of spring 38, so that during the inserting or the pulling apart procedure there is afforded light and rapid assumption and loosening of the latched position.

In FIG. 4 there is also ascertainable, in the region of the handpiece end towards the instrument, a pin 40 providing a security against rotation.

What is claimed is:

1. A tartar-removing dental handpiece comprising:
an elongated gripping sleeve;
a vibratable tartar-removing instrument arranged at one end of the gripping sleeve;
an electrically operable vibration generator arranged in the gripping sleeve to generate vibrations;
means connecting the vibration generator to the tartar-removing instrument to transmit vibrations therebetween;
a current conduit leading to the vibration generator to conduct an electric current thereto;
a cooling medium supply conduit extending through the gripping sleeve for conducting a cooling medium to the tartar-removing instrument;
a coupling member arranged at the end of the gripping sleeve remote from the tartar-removing instrument for connecting the dental handpiece to a cooling medium source and an electric current source, the coupling member including:
 (i) a first connecting conduit for conducting the cooling medium therethrough,
 (ii) a second connecting conduit for conducting electric current therethrough, and
 (iii) a guide trunnion extending into and being rotatable within the gripping sleeve, the guide trunnion being releaseably connected to the gripping sleeve and including a circumferential outer surface;
first and second spaced ring contacts circumferentially extending around and outside of the outer surface of the guide trunnion, the first and second ring contacts being electrically connected to the second connecting conduit;

a first slide contact mounted on the gripping sleeve and extending radially inward into contact with the first ring contact for conducting an electric current between the first ring contact and the current conduit independently of the annular position of the guide trunnion within the gripping sleeve; and a second slide contact mounted on the gripping sleeve and extending radially inward into contact with the second ring contact for conducting an electric current between the second ring contact and the current conduit independently of the annular position of the guide trunnion within the gripping sleeve;

said first and second slide contacts being resiliently biased toward said first and second ring contacts respectively;

an annular passageway formed by the gripping sleeve and the coupling member, extending around the coupling member and in fluid communication with the first connecting conduit and the cooling medium supply conduit for conducting the cooling fluid therebetween, independent of the annular position of the guide trunnion inside the gripping sleeve.

2. A dental handpiece according to claim 1, wherein the tartar-removing instrument is hollow and includes a discharge opening; and the cooling medium supply conduit conducts the cooling fluid into the interior of the tartar-removing instrument and communicates with the discharge opening.

3. A dental handpiece according to claim 1, wherein the coupling member includes at least one regulating member having an externally-actuatable control element for controlling the flow of the cooling medium through the first connecting conduit.

4. A handpiece according to claim 1, wherein the guide trunnion includes a plurality of contiguous sections having different diameters, said sections being arranged with the diameters decreasing towards the front end of the guide trunnion.

5. A handpiece according to claim 1, wherein the vibration generator includes:

a tubular support positioned within the gripping sleeve, coaxial therewith;

an exciter winding wound around the outside of the tubular support and connected to the current conduit; and an electro-magnetic converter connected to the vibration transmission means and extending into the tubular support, coaxial therewith, to generate vibrations.

6. A dental handpiece according to claim 1 wherein:

the gripping sleeve includes a rear tubular member having a sidewall defining an axially extending socket receiving the guide trunnion;

the sidewall includes first and second axially spaced openings radially extending through the sidewall;

the first slide contact radially extends through the first opening and into pressure contact with the first ring contact; and the second slide contact radially extends through the second opening and into pressure contact with the second ring contact.

7. A dental handpiece according to claim 1 wherein the gripping sleeve includes means releasably holding the guide trunnion in the gripping sleeve, said holding means including means exerting radially inward pressure against the guide trunnion to hold the guide trunnion in the gripping sleeve against axial movement.

8. A dental handpiece according to claim 7 wherein:
the guide trunnion includes an outside groove; and
the means exerting pressure against the guide trunnion includes (i) means seating in said outside groove of the guide trunnion, and (ii) spring means engaging said seating means and forcing said seating means into radial pressure contact with the guide trunnion.

9. A tartar-removing dental handpiece comprising:
an elongated gripping sleeve;

a vibratable tartar-removing instrument arranged at one end of the gripping sleeve;

a pneumatically operable vibration generator arranged in the gripping sleeve to generate vibrations;

means connecting the vibration generator to the tartar removing instrument to transmit vibrations therebetween;

a compressed-air conduit extending through the gripping sleeve to the vibration generator for conducting compressed air thereto;

a cooling medium supply conduit extending through the grippin sleeve to conduct a cooling medium to the tartar-removing instrument;

a coupling member arranged at the end of the gripping sleeve remote from the tartar-removing instrument to connect the dental handpiece to a cooling medium source and a compressed-air source, the coupling member including (i) a first connecting conduit for conducting the cooling medium therethrough, (ii) a second connecting conduit for conducting compressed-air through the coupling member and, (iii) a guide trunnion extending into and being rotatable within the gripping sleeve and being releasably connected to the gripping sleeve;

a first pair of spaced sealing rings mounted on and extending around the guide trunnion and engaging the gripping sleeve, the first pair of sealing rings, the guide trunnion and the gripping sleeve forming a first annular passage in communication with the cooling medium supply conduit and the first connecting conduit to conduct the cooling medium therebetween independent of the annular orientation of the guide trunnion within the gripping sleeve; and a second pair of spaced sealing rings mounted on and extending around the guide trunnion and engaging the gripping sleeve, the second pair of sealing rings, the guide trunnion and the gripping sleeve forming a second annular passage in communication with the compressed-air conduit and the second connecting conduit to conduct compressed-air therebetween independent of the annular orientation of the guide trunnion within the gripping sleeve;

the gripping sleeve including a rear member defining an axially extending socket receiving the guide trunnion;

the compressed air conduit including
(i) a first tubular portion extending around, and forming a radial space with, the rear member of the gripping sleeve to receive compressed air from the second annular passage and guide the compressed air forwardly therefrom past the rear member, and (ii) a conical portion extending forward from the first tubular portion to guide the compressed air radially inwardly therefrom and radially inside the vibration generator.

10. A handpiece according to claim 9 wherein:
   the tartar-removing instrument is hollow and includes a discharge opening; and
   the cooling medium supply conduit conducts the cooling fluid into the interior of the tartar-removing instrument, into communication with the discharge opening.

11. A handpiece according to claim 9 wherein the coupling member includes at least one regulating member having an externally-actuatable control element, for controlling the flow of the cooling medium through the first connecting conduit.

12. A handpiece according to claim 9 wherein the guide trunnion includes a plurality of contiguous sections, the sections having different diameters, and being arranged with the diameters decreasing toward a front end of the guide trunnion.

13. A dental handpiece according to claim 9 wherein:
   the compressed air conduit includes a back opening; and
   a rear end of the cooling medium supply conduit is connected to the rear member of the gripping sleeve and extends forward therefrom, through the back opening of the compressed air conduit through the interior thereof.

14. A dental handpiece according to claim 13 wherein the gripping sleeve includes a curved surface forming an outside boundary of the second annular passage to guide compressed air forward therefrom, into the back opening of the compressed air conduit.

* * * * *